U S009671167B1

(12) United States Patent
Bacik et al.

(10) Patent No.: US 9,671,167 B1
(45) Date of Patent: Jun. 6, 2017

(54) PROCESS FOR REDUCING THE TEMPERATURE OF AN EFFLUENT STREAM FLOWING OUT OF A STERILIZATION CHAMBER

(71) Applicant: American Sterilizer Company, Mentor, OH (US)

(72) Inventors: Michael Bacik, Fairview, PA (US); Shadruz Daraie, Fairlawn, OH (US); Peter J. Buczynski, Girard, PA (US)

(73) Assignee: American Sterilizer Company, Mentor, OH (US)

( * ) Notice: Subject to any disclaimer, the term of this patent is extended or adjusted under 35 U.S.C. 154(b) by 105 days.

(21) Appl. No.: 14/940,231

(22) Filed: Nov. 13, 2015

(51) Int. Cl.
*F28C 3/04* (2006.01)

(52) U.S. Cl.
CPC ....................... *F28C 3/04* (2013.01)

(58) Field of Classification Search
CPC ........................................ F28C 3/04
See application file for complete search history.

(56) References Cited

U.S. PATENT DOCUMENTS

| 4,822,563 A * | 4/1989 | Joslyn ................... A61L 2/20 |
| | | 422/31 |
| 8,865,087 B2 | 10/2014 | Buczynski |
| 2015/0305818 A1 | 10/2015 | Butrick |
| 2015/0320896 A1 | 11/2015 | Amor et al. |

FOREIGN PATENT DOCUMENTS

| EP | 0654274 | 5/1995 |
| WO | 9926667 | 6/1999 |
| WO | 0059553 | 10/2000 |
| WO | 2013052287 | 4/2013 |
| WO | 2013093700 | 6/2013 |
| WO | 2014028063 | 2/2014 |
| WO | 2015143008 | 9/2015 |

OTHER PUBLICATIONS

International Search Report and Written Opinion of the International Searching Authority, Application No. PCT/US2016/033397, mailed Sep. 23, 2016.

* cited by examiner

*Primary Examiner* — Regina M Yoo
(74) *Attorney, Agent, or Firm* — Renner, Otto, Boisselle & Sklar, LLP

(57) ABSTRACT

This invention relates to a process for reducing the temperature of an effluent stream flowing out of a sterilization chamber. The process involves the use of a mixing tank and heat exchangers which provide for cooling the effluent to a temperature required by local drain or sewer requirements (e.g., below about 60° C.) while saving on the amount of cooling water needed to cool the effluent.

19 Claims, 3 Drawing Sheets

PROCESS FOR REDUCING THE TEMPERATURE OF AN EFFLUENT STREAM FLOWING OUT OF A STERILIZATION CHAMBER

TECHNICAL FIELD

This invention relates to sterilization processes and, more particularly, to a process for reducing the temperature of an effluent stream flowing out of a sterilization chamber.

BACKGROUND

Sterilization processes are used to sterilize a variety of articles, including medical instruments, and the like. These processes include steam sterilization processes.

SUMMARY

Effluent streams (e.g., steam or hot water) flowing out of steam sterilization chambers are typically disposed of in drains or local sewer systems. However, according to many local codes, the temperature of the effluent being disposed of in such drains or sewer systems usually must be at a temperature below a pre-determined level, for example, below about 60° C. On the other hand, the temperature of an effluent flowing out of a typical steam sterilization chamber is often in the range from about 100° C. to about 140° C. A standard approach to reducing the temperature of such effluents is to mix the effluent with water in a mixing tank to cool the effluent to a desired level prior to its disposal in a drain or sewer system. A problem with this approach is that it typically requires excessive amounts of water to cool the effluent adequately to allow it to be disposed of in a drain or local sewer system. This invention provides a solution to this problem. An advantage of this invention is that it allows for disposal of sterilization effluents at temperatures that are acceptable by local requirements while at the same time providing for significant reductions in cooling waters required for such disposal.

This invention relates to a process for reducing the temperature of an effluent stream flowing from a sterilization chamber, comprising: (A) flowing the effluent stream from the sterilization chamber through a first heat exchanger and a vacuum pump into a mixing tank, the effluent stream flowing from the sterilization chamber being a first stream, the first stream, which comprises water and/or steam, being cooled in the first heat exchanger; (B) flowing a second stream, which comprises water, from the mixing tank through a second heat exchanger, the second stream being cooled in the second heat exchanger; (C) flowing the second stream from the second heat exchanger to and through the first heat exchanger into the mixing tank, the second stream exchanging heat with the first stream in the first heat exchanger; (D) flowing a third stream, which comprises water, through the vacuum pump into the mixing tank; and (E) flowing a fourth stream, which comprises water, out of the mixing tank.

In an embodiment, part of the second stream flowing from the second heat exchanger during step (C) is separated from the second stream to form the third stream.

In an embodiment, a fifth stream, which comprises water, is mixed with the second stream flowing from second heat exchanger to the first heat exchanger.

In an embodiment, part of the fifth stream is separated from the fifth stream to form the third stream.

In an embodiment, the first stream further comprises nitrogen, oxygen, or a mixture thereof.

In an embodiment, the mixing tank is equipped with a temperature detector for measuring the temperature in the mixing tank. The temperature detector may be a resistance temperature detector (RTD).

In an embodiment, the second heat exchanger comprises an air cooled heat exchanger.

In an embodiment, the vacuum pump comprises a liquid ring vacuum pump. The third stream flowing through the vacuum pump may be used to form a water ring for operating the vacuum pump.

In an embodiment, a recirculating pump is used to flow the second stream from the mixing tank through the second heat exchanger.

In an embodiment, the temperature of the first stream flowing from the sterilization chamber to the first heat exchanger is in the range from about 100° C. to about 140° C., or from about 100° C. to about 130° C., or from about 100° C. to about 120° C.

In an embodiment, the first stream flows out of the first heat exchanger, the temperature of the first stream flowing out of the first heat exchanger being in the range from about 75° C. to about 115° C., or from about 75° C. to about 105° C.

In an embodiment, the temperature of the second stream flowing out of the second heat exchanger is in the range from about 15° C. to about 60° C., or from about 15° C. to about 50° C., or from about 15° C. to about 40° C.

In an embodiment, the temperature of the second stream flowing from the first heat exchanger to the mixing tank is in the range from about 5 to about 80° C., or from about 40 to about 75° C.

In an embodiment, the temperature of the fifth stream is in the range from about 10° C. to about 40° C., or about 15° C. to about 30° C., or about 18° C. to about 24° C.

In an embodiment, the ratio of the volumetric flow rate of the second stream to the volumetric flow rate of the fifth stream is in the range from about 2 to about 60, or about 4 to about 20.

In an embodiment, the temperature of the fourth stream flowing out of the mixing tank is below about 60° C., or below about 55° C., or below about 50° C. The fourth stream flowing out of the mixing tank may flow into a drain or sewer.

BRIEF DESCRIPTION OF THE DRAWINGS

In the annexed drawings, like references indicate like parts and features.

DETAILED DESCRIPTION

Figure 1:
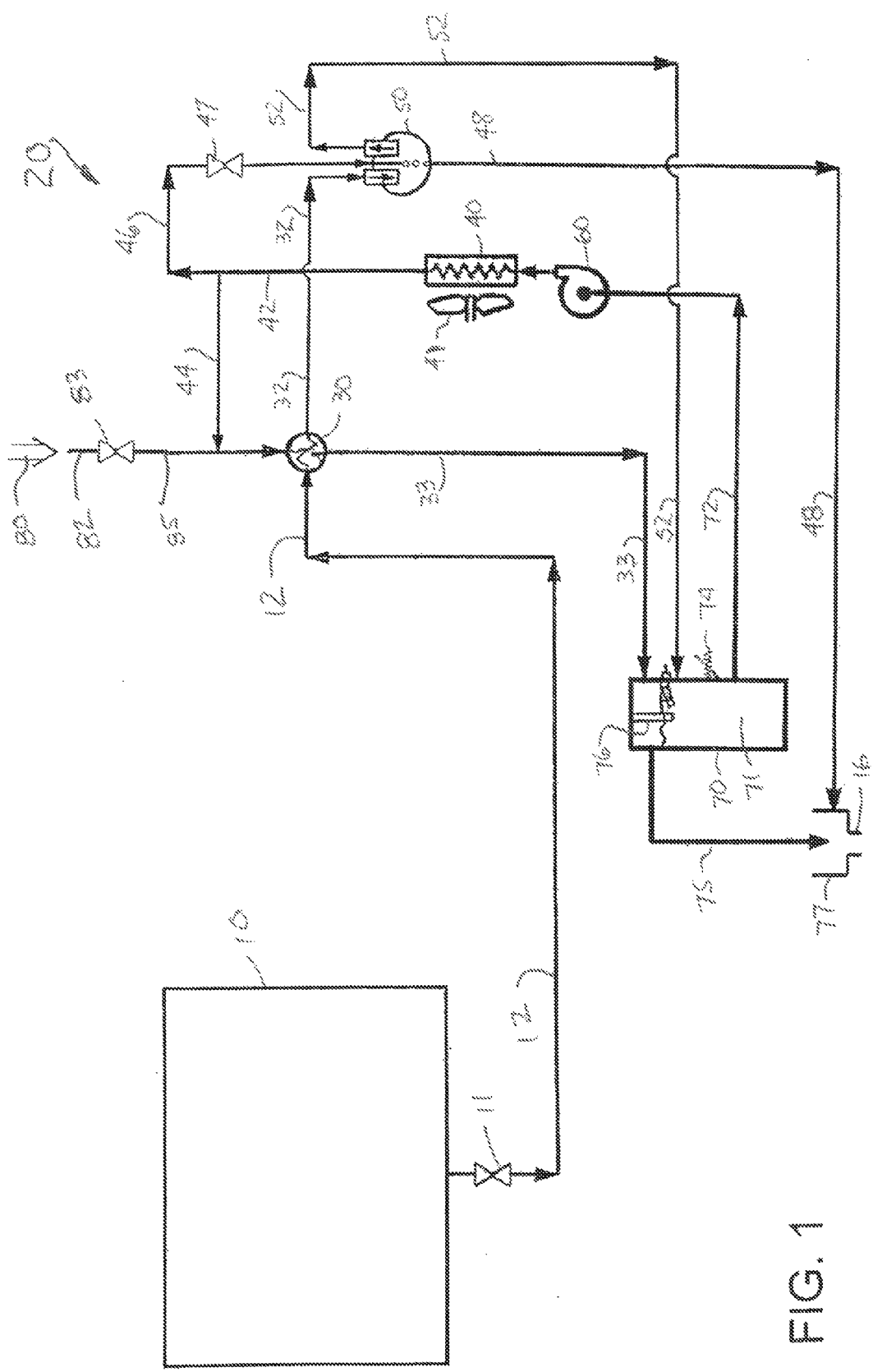
FIG. 1 is a flow sheet showing a process for reducing the temperature of an effluent stream flowing from a sterilization chamber pursuant to the invention.

All ranges and ratio limits disclosed in the specification and claims may be combined in any manner. It is to be understood that unless specifically stated otherwise, references to "a," "an," and/or "the" may include one or more than one, and that reference to an item in the singular may also include the item in the plural.

The phrase "and/or" should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "X and/or Y," when used in conjunction with open-ended language such as "comprising" can refer, in one embodiment, to X without Y (optionally including elements other than Y); in another embodiment, to Y without X (optionally including elements other than X); in yet another embodiment, to both X and Y (optionally including other elements); etc.

The word "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or may refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

The phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of X and Y" (or, equivalently, "at least one of X or Y," or, equivalently "at least one of X and/or Y") can refer, in one embodiment, to at least one, optionally including more than one, X, with no Y present (and optionally including elements other than Y); in another embodiment, to at least one, optionally including more than one, Y, with no X present (and optionally including elements other than X); in yet another embodiment, to at least one, optionally including more than one, X, and at least one, optionally including more than one, Y (and optionally including other elements); etc.

The transitional words or phrases, such as "comprising," "including," "carrying," "having," "containing," "involving," "holding," and the like, are to be understood to be open-ended, i.e., to mean including but not limited to.

The term "sterilization" refers to rendering a substance incapable of reproduction, metabolism and/or growth. The term "sterilization" includes microbial deactivation. While sterilization is often taken to refer to a total absence of living organisms, the term may be used herein to refer to a substance free from living organisms to a degree agreed to be acceptable. Unless otherwise indicated, the term "sterilization" may be used herein to also refer to processes less rigorous than sterilization, for example, disinfection, sanitization, decontamination, cleaning, and the like. Variations of the term "sterilization," such as sterilant, sterilizing, etc., may also be used herein to refer to and encompass related variants associated with sterilization processes as well as processes less rigorous than sterilization (e.g., disinfectant, disinfecting, etc.). The sterilization process may comprise a steam sterilization process.

The term "sterilization chamber" refers to a chamber wherein a sterilization process is conducted. The sterilization chamber may comprise a steam sterilization chamber.

The term "effluent" refers to any fluid (liquid, vapor, or mixture thereof) flowing out of a sterilization chamber that is to be discarded, for example, disposed of in a drain or sewer system. The effluent may comprise steam, hot water (or steam condensate), or a mixture thereof.

Figure 1A:
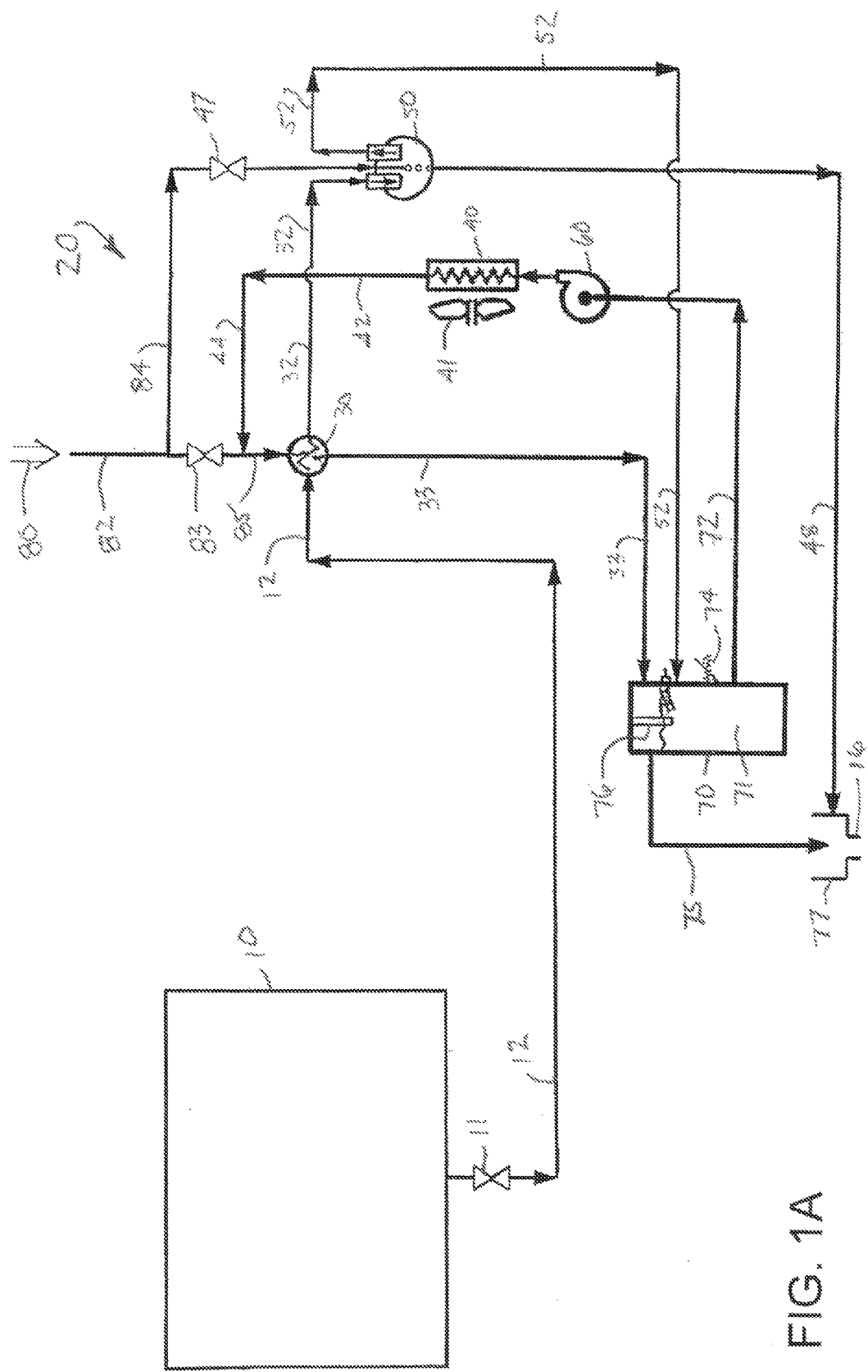
FIG. 1A is a flow sheet showing an alternate embodiment of the process illustrated in FIG. 1.
Figure 2:
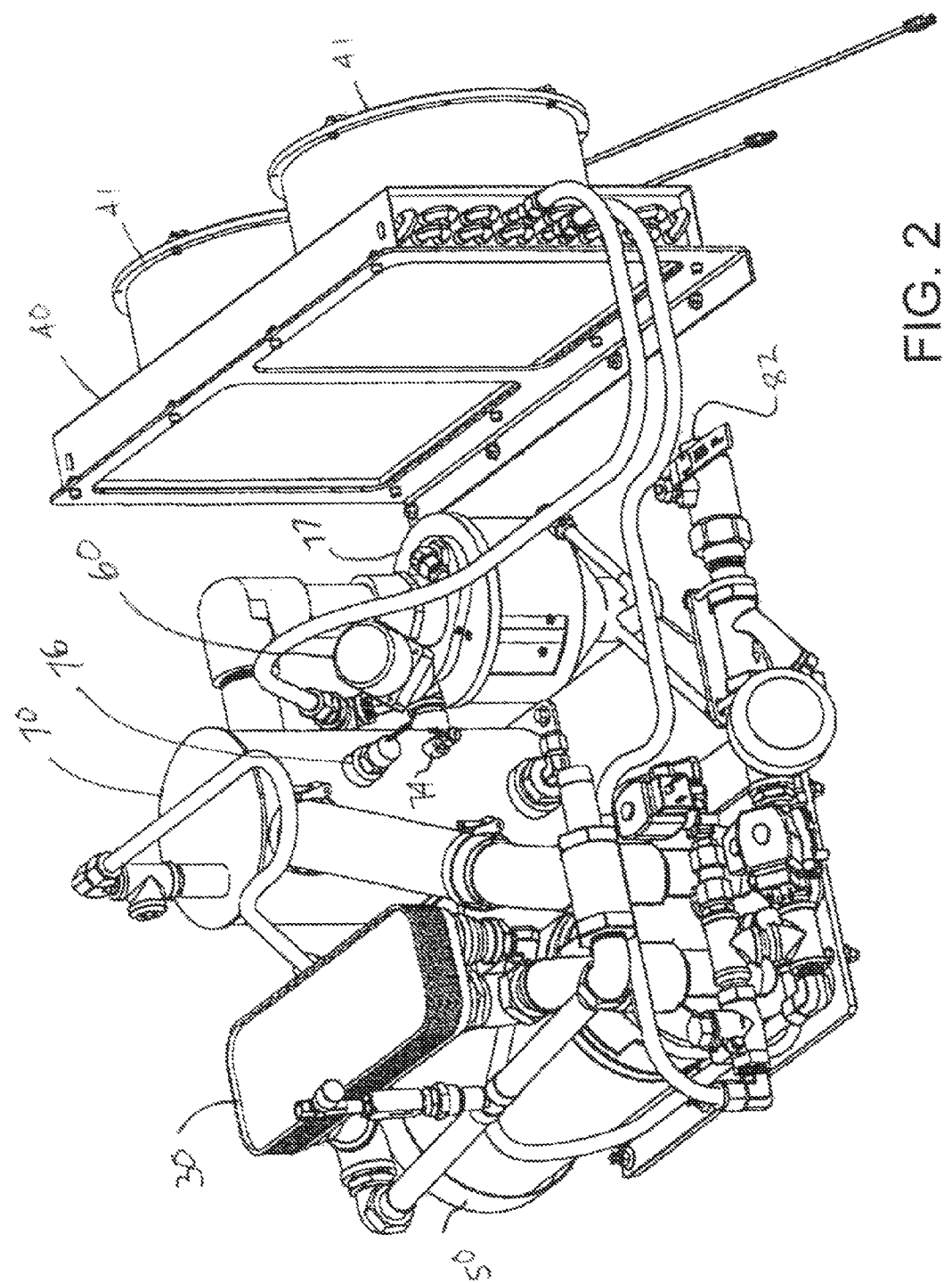
FIG. 2 is a schematic illustration of an apparatus used in the process illustrated in FIG. 1.

Referring to FIGS. 1, 1A and 2, this invention relates to a process for reducing the temperature of an effluent stream flowing from sterilization chamber 10 using effluent cooling system 20.

The sterilization chamber 10 may be of any desired size and design. The sterilization chamber 10 may be a steam sterilization chamber. The internal temperature of the sterilization chamber during the operation of a sterilization cycle may be in the range from about 100 to about 140° C., or from about 100 to about 125° C., or from about 130 to about 140° C. The internal pressure (absolute pressure) within the sterilization chamber 10 during a sterilization cycle may be in the range from about 1 to about 3 atmospheres, or from about 1 to about 2 atmospheres. The internal volume of the sterilization chamber 10 may be of any useful dimension, for example, in the range from about 100 to about 1000 liters, or from about 200 to about 1000 liters.

The effluent flowing out of the sterilization chamber 10 through line 12 may comprise steam, water (e.g., steam condensate), or a mixture thereof. This effluent stream may be referred to as the first stream. The first stream may also contain other fluids, for example, nitrogen, oxygen, or a mixture thereof, and the like. The flow rate of the first stream flowing out of the sterilization chamber 10 through line 12 may be in the range from about 0.05 to about 100 liters per minute (lpm), or from about 0.1 to about 100 lpm, or from about 0.1 to about 80 lpm, or from about 0.1 to about 60 lpm, or from about 0.1 to about 40 lpm. The temperature of the first stream flowing out of the sterilization chamber 10 in line 12 may in the range from about 100° C. to about 140° C., or from about 100° C. to about 125° C., or from about 130° C. to about 140° C.

The effluent cooling system 20 includes first heat exchanger 30, second heat exchanger 40, vacuum pump 50, recirculation pump 60, and mixing tank 70. The first stream flows from the sterilization chamber 10 through valve 11 and line 12 to and through first heat exchanger 30, and from the heat exchanger 30 through line 32 to vacuum pump 50, and from vacuum pump 50 through line 52 to mixing tank 70.

The second stream, which comprises water, flows from mixing tank 70 through line 72 to recirculation pump 60, and then from recirculation pump 60 to and through second heat exchanger 40. Heat exchanger 40 may be an air cooled heat exchanger using fan 41. The second stream is cooled in the second heat exchanger 40 and flows out of the second heat exchanger 40 through line 42. The second stream flowing out of the second heat exchanger 40 through line 42 may have a temperature in the range from about 15° C. to about 60° C., or from about 15° C. to about 50° C., or from about 15° C. to about 40° C., or from about 45° C. to about 60° C. The flow rate of the second stream in line 42 may be in the range from about 15 to about 100 lpm, or from about 15 to about 95 lpm, or from about 15 to about 60 lpm.

The second stream flows from line 42 to and through line 44 to line 85. In an embodiment, the second stream may flow through line 85 to and through first heat exchanger 30, and then through line 33 to mixing tank 70.

In an embodiment (FIG. 1), part of the second stream may be diverted to line 46 where it flows as the third stream through line 46 and valve 47 to vacuum pump 50, and then from vacuum pump 50 through line 52 to mixing tank 70.

In an embodiment, fifth stream 80 may flow through line 82 and valve 83 into line 85 where it may be mixed with the second stream flowing from line 44. The fifth stream may comprise local water or utility water. The fifth stream may have a temperature in the range from about 10 to about 40° C., or about 15 to about 30° C., or about 18 to about 24° C. When the second and fifth streams are mixed, the ratio of the volumetric flow rate of the second stream to that of the fifth stream may be in the range from about 2 to about 60, or from about 4 to about 20.

The second stream, or the second stream mixed with the fifth stream, may flow through line 85 to and through first heat exchanger 30, and then through line 33 to mixing tank 70. The second stream, or the second stream mixed with the fifth stream, flowing through first heat exchanger 30 exchanges heat with the first stream flowing through the first heat exchanger 30. The first stream may be cooled in the first heat exchanger 30. The second stream, or the second stream mixed with the fifth stream, flowing from first heat exchanger 30 through line 33 to mixing tank 70 may have a temperature in the range from about 75 to about 115° C., or from about 75 to about 100° C., or from about 105 to about 115° C. The flow rate of the second stream, or the second stream mixed with the fifth stream, through line 33 may be in the range from about 0.05 to about 100 lpm, or from about 0.1 to about 100 lpm, or from about 0.1 to about 80 lpm, or from about 0.1 to about 60 lpm, or from about 0.1 to about 40 lpm.

Vacuum pump 50 may be used to draw the first stream from the sterilization chamber 10 through valve 11 and line 12. The first stream may flow to and through the first heat exchanger 30, and then from the heat exchanger 30 through line 32 to vacuum pump 50, and then from the vacuum pump 50 through line 52 to mixing tank 70. The vacuum pump 50 may be a liquid ring vacuum pump. In an embodiment (FIG. 1), the third stream may flow from the second heat exchanger 40 through lines 42 and 46 and valve 47 to the vacuum pump 50, and then from the vacuum pump 50 through line 52 to mixing tank 70. In an alternate embodiment (FIG. 1A), part of the fifth stream may be diverted from line 82 to line 84, and flow as the third stream from line 84 through valve 47 to vacuum pump 50, and then from vacuum pump 50 through line 52 to mixing tank 70. The third stream may be used to form a water ring for operating the vacuum pump 50. The flow rate of the third stream through the vacuum pump 50 may be in the range up to about 12 lpm, or from about 1 to about 12 lpm, or from about 1 to about 6 lpm. Vacuum pump 50 may be drained through line 48 and valve 49 when it is not running. Valve 49 may be used to prevent free flow to drain 16.

The mixing tank 70 may have any desired size. For example, the mixing tank 70 may have an internal capacity in the range from about 1 to about 40 liters, or from about 3 to about 38 liters, or from about 3 to about 8 liters, or from about 8 to about 38 liters. The mixing tank 70 may be equipped with a temperature detector 74 for measuring the temperature of the water 71 in the mixing tank 70. The temperature detector 74 may be a resistance temperature detector (RTD). The mixing tank 70 may also be equipped with a liquid level control device 76, which may be of any conventional design. The temperature of the water 71 in mixing tank 70 may be monitored, and if the temperature goes above a pre-determined level (e.g., above about 60° C.), water from the second stream, or the second stream mixed with the fifth stream, from line 33 may be added to the water 71 to bring the temperature of the water 71 down to the required level.

The fourth stream, which comprises water, flows out of the mixing tank 70 through line 75 to drain 16. Line 75 may include a drain funnel 77. The water flowing through line 75 may be referred to as the fourth stream. The temperature of the fourth stream flowing from the mixing tank 70 to drain 16 may be below about 60° C., or below about 55° C., or below about 50° C. The flow rate of the fourth stream may be in the range from 0.05 to about 100 lpm, or from about 0.05 to about 80 lpm, or from about 0.05 to about 60 lpm. The flow rate may be from 0 to about 95 lpm, or from 0 to about 57 lpm.

The mixing tank 70 may be have a relatively large volume, for example, in the range from about 1 to about 40 liters, with a relatively large surface area that is exposed to the ambient air, for example, from about 500 to about 40,000 $cm^2$, or from about 800 to about 32,000 $cm^2$. By using such a large mixing tank with such a large surface area, the water 71 in the mixing tank 70 and the relatively hot water flowing into the mixing tank 70 can be mixed and the temperature of the water 71 in the mixing tank 70 may be allowed to equilibrate relatively quickly. The water 71 in the mixing tank may tend to lose heat through the relatively large surface area of the tank. By using the cooling system 20 in combination with the relatively large mixing tank 70, considerable reductions in water consumption, for example, at least about 20%, or at least about 40%, or at least about 60% or more, per sterilization cycle, may be achieved.

While the invention has been explained in relation to various embodiments, it is to be understood that various modifications thereof will become apparent to those skilled in the art upon reading the specification. Therefore, it is to be understood that the invention disclosed herein includes any such modifications that may fall within the scope of the appended claims.

The invention claimed is:

1. A process for reducing the temperature of an effluent stream from a sterilization chamber, comprising:
   (A) flowing the effluent stream from the sterilization chamber through a first heat exchanger and a vacuum pump into a mixing tank, the effluent stream flowing from the sterilization chamber being a first stream, the first stream, which comprises water and/or steam, being cooled in the first heat exchanger;
   (B) flowing a second stream, which comprises water, from the mixing tank through a second heat exchanger, the second stream being cooled in the second heat exchanger;
   (C) flowing the second stream from the second heat exchanger to and through the first heat exchanger into the mixing tank, the second stream exchanging heat with the first stream in the first heat exchanger;
   (D) flowing a third stream, which comprises water, through the vacuum pump into the mixing tank; and
   (E) flowing a fourth stream, which comprises water, out of the mixing tank.

2. The process of claim 1 wherein part of the second stream flowing from the second heat exchanger during step (C) is separated from the second stream to form the third stream.

3. The process of claim 1 wherein a fifth stream, which comprises water, is mixed with the second stream flowing from second heat exchanger to the first heat exchanger.

4. The process of claim 3 wherein a part of the fifth stream is separated from the fifth stream to form the third stream.

5. The process of claim 3 wherein the temperature of the fifth stream is in the range from about 10° C. to about 40° C.

6. The process of claim 3 wherein the ratio of the volumetric flow rate of the second stream to the volumetric flow rate of the fifth stream is in the range from about 2 to about 60.

7. The process of claim 1 wherein the first stream further comprises nitrogen, oxygen, or a mixture thereof.

8. The process of claim 1 wherein the mixing tank is equipped with a temperature detector for measuring the temperature in the mixing tank.

9. The process of claim 8 wherein the temperature detector is a resistance temperature detector.

10. The process of claim 1 wherein the second heat exchanger comprises an air cooled heat exchanger.

11. The process of claim 1 wherein the vacuum pump comprises a liquid ring vacuum pump.

12. The process of claim 11 wherein the third stream flowing through the vacuum pump forms a water ring for operating the vacuum pump.

13. The process of claim 1 wherein a recirculating pump is used to flow the second stream from the mixing tank to the second heat exchanger.

14. The process of claim 1 wherein the temperature of the first stream flowing from the sterilization chamber to the first heat exchanger is in the range from about 100° C. to about 140° C.

15. The process of claim 1 wherein the temperature of the first stream flowing out of the first heat exchanger is in the range from about 75° C. to about 115° C.

16. The process of claim 1 wherein the temperature of the second stream flowing out of the second heat exchanger is in the range from about 15° C. to about 60° C.

17. The process of claim 1 wherein the temperature of the second stream flowing from the first heat exchanger to the mixing tank is in the range from about 5° C. to about 80° C.

18. The process of claim 1 wherein the fourth stream flowing out of the mixing tank is at a temperature that is below about 60° C.

19. The process of claim 1 wherein the fourth stream flowing out of the mixing tank flows into a drain or a sewer.

* * * * *